United States Patent [19]
Jacobi

[11] Patent Number: 4,720,265
[45] Date of Patent: Jan. 19, 1988

[54] CURVED DIE POSITIONER

[76] Inventor: Richard Jacobi, 229 Wimbledon Rd., Midwest City, Okla. 73130

[21] Appl. No.: 911,760

[22] Filed: Sep. 26, 1986

[51] Int. Cl.⁴ .......................................... A61C 19/00
[52] U.S. Cl. ...................................... 433/74; 264/16
[58] Field of Search ..................... 433/74, 53; 264/16

[56] References Cited

U.S. PATENT DOCUMENTS

| | | | |
|---|---|---|---|
| 3,153,283 | 10/1964 | Weissman | 433/74 |
| 4,054,995 | 10/1977 | Yoshida | 433/74 |
| 4,127,939 | 12/1978 | Samuel et al. | 433/74 |
| 4,238,189 | 12/1980 | Tirino | 433/74 |
| 4,242,812 | 1/1981 | Randoll et al. | 433/74 |
| 4,300,884 | 11/1981 | Camacho | 433/74 |

*Primary Examiner*—John J. Wilson

[57] ABSTRACT

A device and method for forming a removable die within a stone cast of a dental arch is presented. The die is attached to one end of a curved dowel pin which in turn slides into a curved channel in the base of the stone cast. The unique curved path of insertion and removal allow the die to be repositioned accurately and held securely with a single dowel.

5 Claims, 3 Drawing Figures

CURVED DIE POSITIONER

BACKGROUND OF THE INVENTION

The present invention relates in general to stone casts employed in restorative dentistry, and more particularly to a dowel pin for holding a replica of a single tooth (die) within a replica of the dental arch (stone cast) in such a way that the die can be easily removed from the stone cast and accurately repositioned during the fabrication of an artificial crown or other restoration for the tooth.

In the normal procedure for fabricating an artificial crown, an elastic impression is made of the prepared teeth and their surrounding tissues. The impression is filled with dental stone which, when hardened, accurately duplicates the dental structures. The crown can then be fabricated on the stone cast. During fabrication it is necessary to remove the die of the tooth being restored from the cast and trim it to gain access for forming those surfaces which would otherwise be obscured by the replicas of the adjacent teeth and gums. During fabrication of the crown, the die must be repeatedly removed and placed back in the stone cast for proper adjustment and finishing of the contacts with the neighboring teeth. This requires a die that can be easily removed from the stone cast and replaced with a high degree of precision. When seated in the stone cast, the die must resist tipping and rotation.

PRIOR ART

Most present methods of forming removable dies utilize dowel pins that are fixed to the dies and fit into channels in the stone cast. Existing dowels are made in various shapes, but they all follow a straight path of insertion and removal. Samuel et al (U.S. Pat. No. 4,127,939, Dec. 5, 1978) used a J-shaped pin, but the parts of the pin that slide in and out of the base are straight and the die must follow a straight path of insertion and removal. Tirino (U.S. Pat. No. 4,238,189, Dec. 9, 1980) shows a curved attachment to a tapered dowel pin, but the dowel is straight to fit into a straight channel and the curved attachment serves only as a stabilizing aid during pouring of the cast.

To prevent rotation of the die within the stone cast with these systems it is necessary either to use two parallel pins, which require elaborate equipment for their placement, or to place some sort of keyway in the form of a horizontal projection, as shown by Weissman (U.S. Pat. No. 3,153,283) or a flat surface such as described by Yoshida (U.S. Pat. No. 4,054,995) and Tirino (U.S. Pat. No. 4,238,189). In order for such anti-rotation devices to be effective, they must have a relatively great horizontal dimension. This requires that the die have a bulky base which, especially with small teeth, can interfere with the technician's work.

A further disadvantage of straight-path dowel systems is that the small end of the dowel is buried deep within the stone base making it necessary to form a separate access channel through the base so that the die can be pushed out of the cast with an instrument, and to allow the removal of debris which would prevent the dowel from seating completely into its channel. Frequently when casts are mounted on hinged articulators, vertical access channels are blocked by a member of the articulator and an additional horizontal channel providing access from the side of the stone base is necessary. This is not only time consuming to form, but requires the placement of an instrument within the channel each time the die is removed.

Numerous manufacturers employ sleeves into which the dowel pins fit in order to facilitate positioning of the dowel within the impression prior to pouring the stone cast or to facilitate removal from the hardened cast. If the sides of a dowel are sufficiently tapered, it will separate from the stone cast without use of a sleeve. Camacho (U.S. Pat. No. 4,300,884, Nov. 17, 1981) shows a system of notched ribs, rods, and spherical coupling members used to support the dowel pin during pouring of the stone cast. Here, again, the removable dowel is straight and fits into a straight, tapered channel, depending on a flattened side to prevent rotation.

SUMMARY

The basic element of this invention consists of a curved dowel pin to be used to removably join a dental die to a stone cast of the dental arch. It is superior to the prior art devices in the following respects: 1. Its curvature provides greater stability against rotation than does the flat side of a straight pin. 2. Unlike systems using keyways and double pins, it's attachment to the die need be no wider than the tooth which the die represents. This facilitates trimming and finishing of the crown margins. 3. The small and of the curved pin protrudes from the side, rather than from the bottom of the stone cast. This eliminates the need for forming an additional access channel for pushing the die out and for removing debris from the dowel's channel. 4. The curvature brings part of the pin close to the rim of the the impression to which it can be securely anchored for pouring of the cast without elaborate positioning devices.

DESCRIPTION OF THE PREFERRED EMBODIMENT

Figure 1:
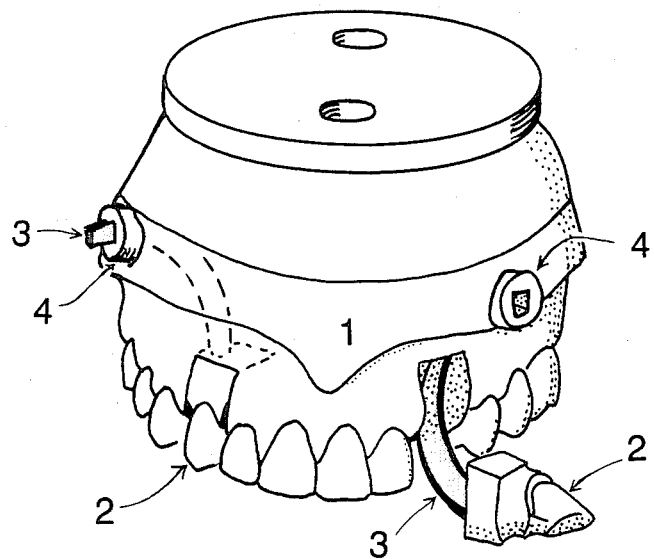
FIG. 1 is an anterior perspective view of a stone cast of a dental arch 1 with two removable dies 2 attached to curved dowel pins 3. Two sleeves 4 are embedded in the cast to hold the curved dowels. The die on the viewer's left is seated in the stone cast and the die on the viewer's right is partially removed.
Figure 2:
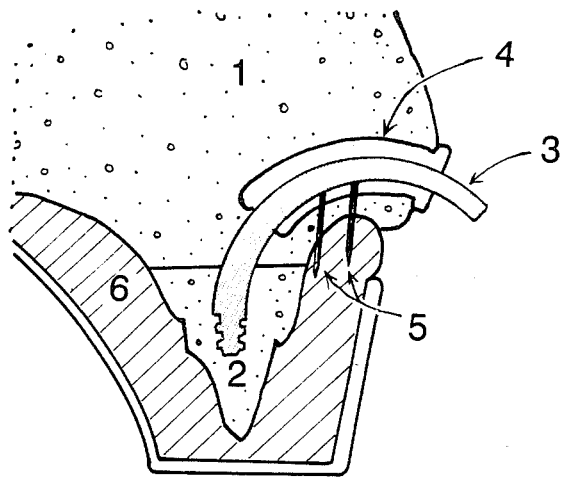
FIG. 2 shows a cross section of part of a stone cast, die, and curved dowel pin assembly with two retaining pins 5 before separation from the impression 6 in which the stone has been cast.
Figure 3:
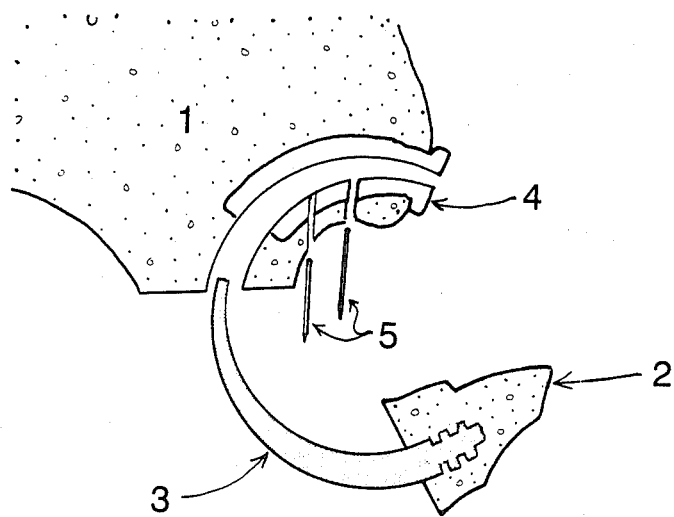
FIG. 3 is a cross section representing the same plane shown in FIG. 2 with the die and the retaining pins removed from the dental cast.

The invention is depicted in FIGS. 1, 2, and 3. Its essential part is a curved metal dowel pin 3. The larger end of the dowel is notched so that it will be firmly and inseprarably embedded in the stone which forms the die of the tooth being restored 2 as shown in FIGS. 2 and 3. A rigid sleeve 4 fits snugly around part of the smooth shank of the dowel. The dowel 3 is free to move in and out of the sleeve 4 along a curved path as shown in FIG. 3.

The curved dowel 3 can be attached to the die 2 by either of two methods:

Method A. Before the impression is poured, the sleeve 4 containing the curved dowel pin 3 is attached to the impresion 6 by inserting one or more of the retaining pins 5 into the periphery of the impression 6 as shown in FIG. 2. The notched head of the dowel should be centered within the impression of the tooth to be restored. Any retaining pins 5 which do not fit into the wall of the impression 6 may be removed at this time. The impression 6 is then poured with a die stone to a level a few millimeters above the necks of all teeth and the stone is allowed to harden. The hardened stone around the curved dowel is coated with a separating agent such as petroleum jelly and the remainder of the impression is filled with dental stone, covering all of the curved dowel 3 and its sleeve 4 except for the small end, which is left protruding from the cast. When the stone is hard, the cast is removed from the impression and any retaining pins 5 projecting from the cast are removed.

Method B. Frequently the laboratory technician will receive from the dentist a hardened stone cast rather than an impression. In these cases the curved dowel 3 can be attached to the previously formed stone cast by grinding the base of the case flat to within a few millimeters of the necks of all the teeth. A vertical hole is then bored into the flattened base directly over the replica of the tooth being treated. The head of the dowel is inserted into the bored hole with the smaller end of the dowel curving away in a vertical facial-lingual plane, and bonded to the cast with cement. Here no retaining pins 5 are used and use of a sleeve 4 is optional. The exposed surface of the curved dowel pin 3 and the stone immediately surrounding it are coated with a separating agent and a stone base 1 is poured covering the remainder of the dowel and sleeve except for one or two millimeters of the smaller end.

The procedure for completing the removable-die assembly from this point is the same regardless of whether method A or method B has been used: Vertical saw cuts are made on both sides of the die 2 in planes roughly parallel to that of the curved dowel. The cuts are extended just through the layer of separating agent to free the die 2 from the remainder of the cast 1. The die is removed from the cast by tapping on the small end of the dowel 3 that protrudes from the cast 1. The die can than be trimmed to the prepared finish lines without interference from the attachment between dowel pin and die. An artificial crown can then be fabricated in the usual manner. The die can be repeatedly replaced and removed from the stone cast with gentle finger pressure. Any small chips of stone or wax which may fall into the channel can be easily removed by a stream of compressed air directed into the channel. When fully inserted into its channel the curved dowel effectively resists tipping and rotation which would jeopardize the accuracy of the restoration.

Multiple Curved Path Dowel Pins can be placed simultaneously when more than one tooth is being treated, or to allow removal of other segments of the cast.

What is claimed is:

1. A curved metal dowel pin for removably joining a dental die to a dental cast, said dowel having a notched or knurled head at one end for embedding in said die, and a smooth shank extending from said head and being uniformly curved substantially throughout its length for sliding into a similarly shaped channel in said dental cast, said shank terminating in a tip which is smaller in diameter than the entrance of the channel.

2. A curved dowel pin as in claim 1 in combination with one or more retaining pins, said dowel pin having one or more holes drilled into its shank to receive said retaining pins in such a way that the retaining pins project inside the curve of said dowel pin for attachment of said curved dowel pin to a dental impression.

3. A curved dowel pin as in claim 1 in combination with a sleeve and one or more retaining pins, said sleeve having a longitudinal curved channel to receive the curved shank of the dowel pin and one or more transverse perforations from which said retaining pins project and are generally parallel to the plane of curvature, to each other, and to the head of the curved dowel pin.

4. A method of forming a removable dental die comprising the steps of:
   (a) positioning a curved dowel pin, having a head and a shank extending from said head and being uniformly curved throughout its length, over a dental impression with the head of the dowel pin inside the impression of the selected tooth and securing said curved dowel pin to the impression by means of one or more retaining pins with one end of each attached to the curved dowel and the other end inserted into the border of the impression.
   (b) pouring die-forming material into the impression so that it slightly overfills the impressions of the teeth and covers the notched head of the curved dowel,
   (c) coating the exposed shank of the curved dowel and the surrounding hardened die material with a separating agent, such as petrolatum,
   (d) filling the rest of the impression with dental stone so that it covers the shank of the curved dowel except for its tip,
   (e) separating the die from the rest of the hardened stone cast by sawing through the die material on either side of the replica of the selected tooth to the level of the separating agent and tapping the small protruding end of the curved dowel.

5. A method of forming a removable dental die comprising the steps of:
   (a) pouring a die-formng material into a dental impression to a level a few millimeters above the necks of the teeth,
   (b) drilling a hole in the top of the hardened die material directly over the replica of the tooth being treated,
   (c) providing a curved dowel pin having a head and a shank extending from said head and being uniformly curved substantially throughout its length,
   (d) cementing the head of said curved dowel pin into the previously drilled hole so that the shank of the dowel curves upward and laterally,
   (e) coating the shank of the curved dowel and the surrounding die material with a separating agent,
   (f) pouring a base of dental stone on top of the die material so that the curved dowel is completely covered except for its tip which is left protruding from the side of the base,
   (g) separating the die from the rest of the hardened stone cast by sawing through the die material on either side of the replica of the selected tooth to the level of the separating agent and tapping the small protruding end of the curved dowel.

* * * * *